(12) United States Patent
Ye et al.

(10) Patent No.: US 11,619,621 B2
(45) Date of Patent: Apr. 4, 2023

(54) APPLICATION OF ELECTROCHEMICAL IMPEDANCE SPECTROSCOPY IN DRILLING FLUID COMPOSITION MEASUREMENTS

(71) Applicant: Halliburton Energy Services, Inc., Houston, TX (US)

(72) Inventors: Xiangnan Ye, Cypress, TX (US); Li Gao, Katy, TX (US); Dale E. Jamison, Humble, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 1051 days.

(21) Appl. No.: 16/321,006

(22) PCT Filed: Aug. 24, 2016

(86) PCT No.: PCT/US2016/048349
§ 371 (c)(1),
(2) Date: Jan. 25, 2019

(87) PCT Pub. No.: WO2018/038717
PCT Pub. Date: Mar. 1, 2018

(65) Prior Publication Data
US 2019/0227048 A1 Jul. 25, 2019

(51) Int. Cl.
*G01N 27/02* (2006.01)
*G01N 33/28* (2006.01)
(Continued)

(52) U.S. Cl.
CPC ....... *G01N 33/2823* (2013.01); *E21B 21/062* (2013.01); *E21B 49/086* (2013.01); *G01N 27/026* (2013.01); *G01N 27/028* (2013.01)

(58) Field of Classification Search
CPC ............... G01N 27/028; G01N 27/026; G01N 33/2823; E21B 21/062; E21B 49/086
See application file for complete search history.

(56) References Cited

U.S. PATENT DOCUMENTS 4,822,456 A * 4/1989 Bryan ............... G01N 27/4165
205/794.5
7,088,115 B1 8/2006 Glenn et al.
(Continued)

FOREIGN PATENT DOCUMENTS

WO 2009031088 3/2009
WO 2009130325 10/2009
(Continued)

OTHER PUBLICATIONS

Canadian Office Action for Application No. 3,028,979 dated Dec. 13, 2019.
(Continued)

*Primary Examiner* — Alesa Allgood
(74) *Attorney, Agent, or Firm* — Thomas Rooney; C. Tumey Law Group PLLC (57) ABSTRACT

Systems and methods are described herein. The method generally includes generating frequency responses of one or more sample fluids having known fluid properties, selecting an equivalent circuit model for modeling the frequency responses, the equivalent circuit model including one or more model elements, calculating an equivalent impedance of the equivalent circuit model, generating a correlation between the one or more model elements and the known fluid properties, measuring an impedance of a drilling fluid, and determining at least one property of the drilling fluid based on the correlation between the one or more model elements and the known fluid properties.

17 Claims, 7 Drawing Sheets

(51) Int. Cl.
*E21B 49/08* (2006.01)
*E21B 21/06* (2006.01)

(56) References Cited

U.S. PATENT DOCUMENTS

| | | | |
|---|---|---|---|
| 2002/0178805 | A1 | 12/2002 | Difoggio et al. |
| 2005/0179449 | A1* | 8/2005 | Wooton ............. G01N 33/2888 |
| | | | 324/691 |
| 2005/0184734 | A1 | 8/2005 | Sosnowski et al. |
| 2006/0214671 | A1* | 9/2006 | Wooton ............... G01N 27/026 |
| | | | 324/698 |
| 2014/0182363 | A1 | 7/2014 | Potyrailo et al. |
| 2015/0211350 | A1* | 7/2015 | Norman ................. E21B 47/10 |
| | | | 702/9 |
| 2016/0341587 | A1* | 11/2016 | Huang ................... E21B 47/00 |

FOREIGN PATENT DOCUMENTS

| | | |
|---|---|---|
| WO | 2015199659 | 12/2015 |
| WO | 2016099489 | 6/2016 |
| WO | 2016160021 | 10/2016 |

OTHER PUBLICATIONS

Int. J. Electrochem. Sci., 8 (2013 4384-4396, Electrochemical Impedance Spectroscopy Behaviour of Guanine on Nanostructured Planar Electrode, Int'l Journal of Electrochemical Science, Apr. 1, 2013.
International Search Report and Written Opinion for PCT/US2016/048349 dated Aug. 24, 2016.

\* cited by examiner

FIG. 10

APPLICATION OF ELECTROCHEMICAL IMPEDANCE SPECTROSCOPY IN DRILLING FLUID COMPOSITION MEASUREMENTS

BACKGROUND

During the drilling of a wellbore into a subterranean formation, a drilling fluid, also referred to as a drilling mud, may be continuously circulated from the well surface down to the bottom of the wellbore being drilled and back to the well surface again. The drilling fluid may include a mixture of water, oil, additives (e.g., viscosifiers, weighting materials, and the like), and combinations thereof, to impart certain properties to the drilling fluid to satisfy different drilling requirements.

The drilling fluid can serve several functions, one of them being to transport wellbore cuttings up to the surface where they are separated from the drilling fluid. Another function of the drilling fluid can include providing hydrostatic pressure against the wall of the drilled wellbore, thereby preventing wellbore collapse and the resulting influx of gas or liquid from the formations being penetrated. For these and other reasons, it can be important to know the characteristics and chemical composition of the drilling fluid during circulation.

For instance, when using an oil-based drilling fluid, knowledge of the oil/water ratio in the drilling fluid allows a drilling operator to determine the fluid rheology, the impact the drilling fluid may have on the formation, the salinity of the drilling fluid, density, filtration characteristics or requirements, and the like. A drilling fluid that is too viscous may reduce drilling efficiency. Conversely, a drilling fluid that is not viscous enough may be lost to the formation.

Drilling fluid compositions may also vary during drilling operations due to the accumulation of wellbore cuttings. The wellbore cuttings may be low gravity solids (LGS) (e.g., solids having a size less than 8-10 microns) and have a lower density than the weighting materials in the drilling fluid. The LGS can significantly affect the drilling fluid properties. For example, when the content of the LGS is too high, the drilling fluid can deteriorate to the point where it becomes unusable. At such a point, costly treatment may be introduced into the wellbore to recover the drilling fluid or the whole volume of affected drilling fluid is removed from the wellbore. Thus, to ensure successful drilling operations without interruption, it is critical to monitor the drilling fluid properties while it is circulating through the wellbore.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Embodiments disclosed herein are directed to systems and methods for determining drilling fluid properties, including oil/water ratio (OWR), low gravity solids (LGS) content, mud density, brine salinity, and the like, and, more particularly, to indirectly determine drilling fluid properties using electrochemical impedance spectroscopy (EIS) techniques. EIS is a non-invasive technique for measuring properties of a medium as a function of frequency (also referred to as the excitation frequency). Although the EIS technique is described herein with reference to drilling fluid or "mud," the properties of other fluids or fluid types can also be determined using the presently described EIS techniques.

The drilling fluid may comprise any emulsion of oil and water (e.g., an oil-based mud) desired to be analyzed, such as emulsions at a wellsite. An oil-based mud is a drilling fluid in which the continuous phase is a non-aqueous fluid and the internal phase is an aqueous fluid. "Water" as used herein, refers to any aqueous fluid, and more generally to any fluid that is immiscible with the oil, and is used for the internal phase of the drilling fluid. Examples of water include fresh water, salt water, brines, or any other fluid that is immiscible with the continuous phase. "Oil," likewise, as used herein refers to any non-aqueous fluid used for the continuous phase of the drilling fluid. Examples of non-aqueous fluids may include hydrocarbon liquids or products derived therefrom. Further, the term "non-aqueous fluid" also encompasses synthetic muds or any non-aqueous fluid that is analogous to oil muds and may be analyzed using the methods and systems described herein.

The drilling fluid may additionally comprise drilling fluid additives, such as, viscosifiers, emulsifiers, density modifiers, and weighting materials (e.g., barite), lubricants, shale inhibitors, fluid loss additives, lost circulation material (e.g., ground peanut shells, mica, cellophane, walnut shells, calcium carbonate, plant fibers, cottonseed hulls, ground rubber, polymeric materials), and the like. During circulation in the wellbore, solids such as pieces of the formation, wellbore cuttings, and other types of solids found in a wellbore, may be introduced into the drilling fluid. The solids may be of a variety of sizes and shapes.

The circulating drilling fluid may be analyzed as described herein to determine one or more fluid properties such as, OWR, LGS weight, mud density, brine salinity, and the like. However, other drilling circulating fluid properties such as viscosity, plastic viscosity, yield point, gel strength, filtration loss, lubricity, pH, sand content, electrical stability, and the like can also be determined using the methods and systems described herein. While referred to herein as circulating drilling fluid properties, it is contemplated that in certain circumstances, the embodiments described herein may be utilized to analyze non-circulating drilling fluid, such as analysis of the drilling fluid prior to introduction into the wellbore or upon retrieval of the drilling fluid from the wellbore.

Prior to analyzing and/or determining the properties of the drilling fluid obtained from a wellsite, laboratory tests are initially performed to determine the effect of frequency on the impedance of sample drilling fluids having known fluid properties such as OWR, LGS weight, mud density, and brine salinity. For testing purposes, the sample drilling fluids may be drilling muds prepared using the XP-07™ synthetic paraffin base fluid available from Halliburton Energy Services of Houston, Tex. However, it should be noted that the laboratory testing may utilize different kinds of base fluids depending on the base fluid in the drilling muds used in drilling operations. In addition, for testing purposes, the low gravity solids (LGS) present in the drilling fluids may be simulated using REV DUST® (an artificial drill solid available from Milwhite Inc., of Houston Tex.). However, other materials that can simulate the low gravity solids present in the drilling fluids can also be used, without departing from the scope of the disclosure.

Typically, impedance $Z(\omega)$ of a fluid at an angular frequency $\omega=2\pi f$ is given by $Z(\omega)=Z'(\omega)+iZ''(\omega)$, where $Z'(\omega)$ is the real part (i.e., resistance) of the impedance and $Z''(\omega)$ is the imaginary part (i.e., reactance) of the impedance. The variation in the impedance due to variation in the angular frequency can be represented using a Nyquist plot.

FIGS. 1-4 are Nyquist plots illustrating the frequency responses of the sample drilling fluids for different values of OWR, LGS weight, mud density, and brine salinity. Specifically, FIGS. 1-4 depict the variation in the impedance of the sample drilling fluids due to variation in the angular frequency. In each of FIGS. 1-4, the resistance is represented on the abscissa and the reactance is represented on the ordinate, and the angular frequency is varied from about 20 Hz to about 100 kHz. However, the range of frequency is not limited thereto and the angular frequency may be varied across a desired range of frequency and ideally from 0 Hz to infinity ($\infty$). Also, in FIGS. 1-4, the REV DUST® weight that is used to simulate the LGS weight in drilling fluids is represented as RD.

Figure 1:
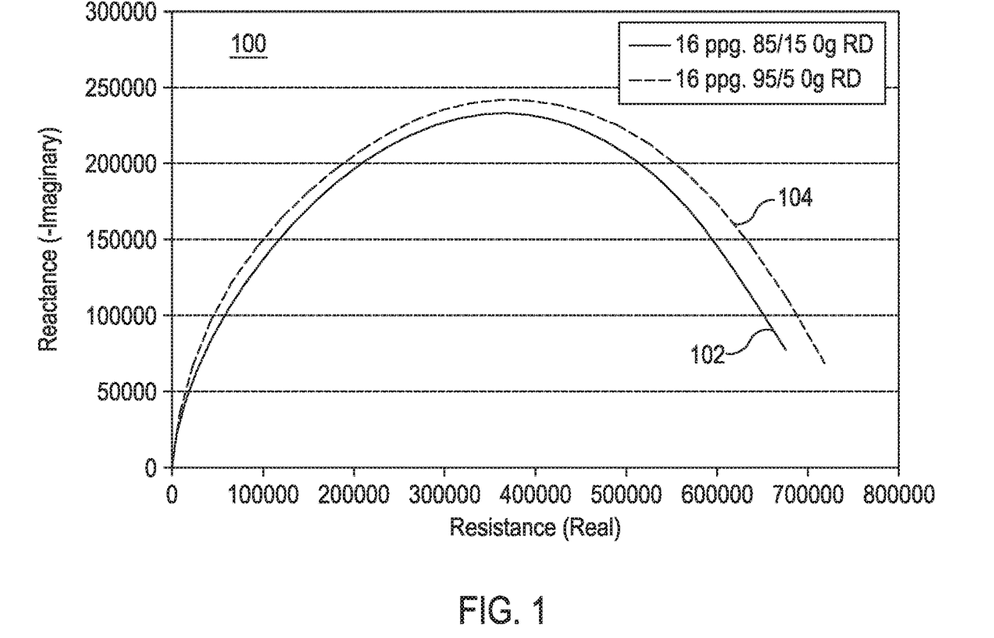
FIG. 1 illustrates Nyquist plots of the frequency responses of two sample drilling fluids having different oil/water ratios.

In FIG. 1, the Nyquist plot 100 depicts a curve 102 and a curve 104 representative of two sample drilling fluids having different OWR. Specifically, the curve 102 depicts the variation in the impedance due to a drilling fluid having an OWR of around 85/15 and the curve 104 depicts the variation in the impedance due to a drilling fluid having an OWR of around 95/5. Both drilling fluids have a mud density of around 16 pounds per gallon (ppg) (about 1917.222 gram per liter) and an LGS weight of 0 g.

Figure 2:
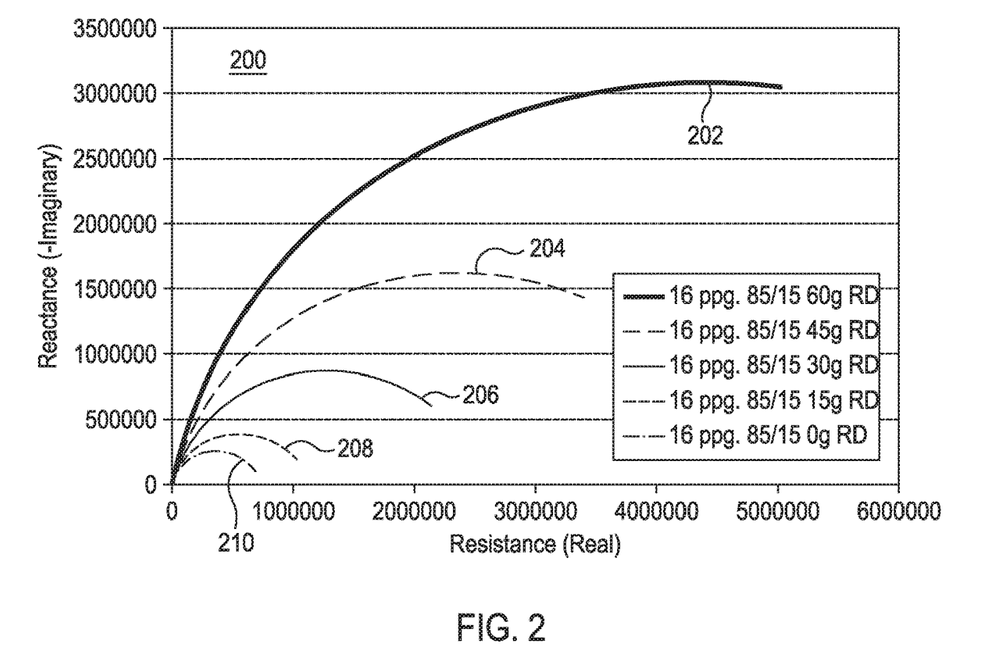
FIG. 2 illustrates Nyquist plots of the frequency responses of five sample drilling fluids each having different REV DUST® weights to simulate different weights of low gravity solids.

FIG. 2 illustrates a Nyquist plot 200 showing curves 202, 204, 206, 208, and 210 representative of five sample drilling fluids each having different REV DUST® weights to simulate different weights of LGS. As illustrated, the curve 202 depicts a variation in the impedance of a drilling fluid having a LGS weight of around 60 g, the curve 204 depicts a variation in the impedance of a drilling fluid having a LGS weight of around 45 g, the curve 206 depicts a variation in the impedance of a drilling fluid having a LGS weight of around 30 g, the curve 208 depicts a variation in the impedance of a drilling fluid having a LGS weight of around 15 g, and the curve 210 depicts a variation in the impedance of a drilling fluid having LGS weight of 0 g. In FIG. 2, each sample drilling fluid has a mud weight of around 16 ppg and an OWR of around 85/15.

Figure 3:
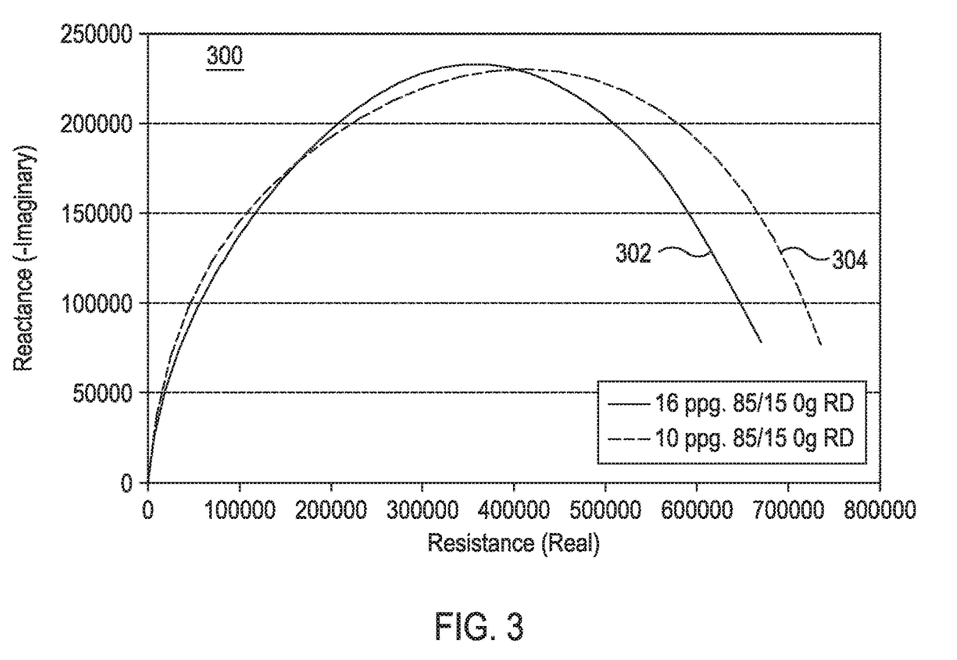
FIG. 3 illustrates Nyquist plots of the frequency responses of two sample drilling fluids having different mud densities.

FIG. 3 illustrates a Nyquist plot 300 showing curves 302 and 304 representative of two sample drilling fluids having different mud densities. As illustrated, the curve 302 depicts a variation in the impedance due to a drilling fluid having a mud density of around 16 ppg and the curve 304 depicts a variation in the impedance due to a drilling fluid having a mud density of around 10 ppg (about 1198.264 gram per litre). Each of the drilling fluid samples has an OWR of around 85/15 and a LGS weight of 0 g.

Figure 4:
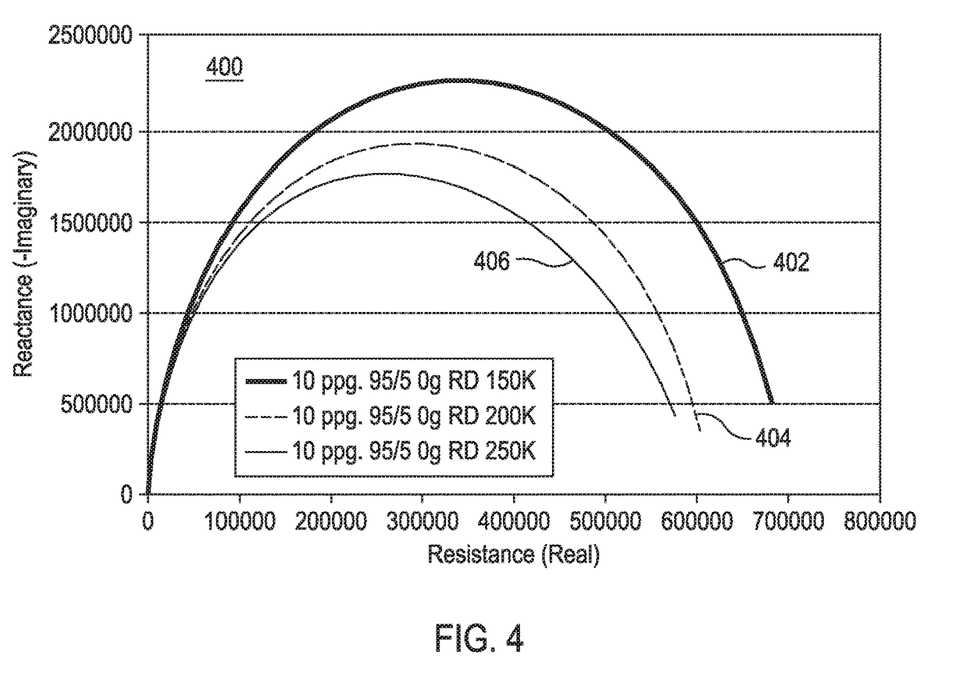
FIG. 4 illustrates Nyquist plots of the frequency responses of three sample drilling fluids having different brine salinities.

FIG. 4 illustrates a Nyquist plot 400 showing curves 402, 404, and 406 representative of three sample drilling fluids having different brine salinities. As illustrated, the curve 402 depicts a variation in the impedance due to a drilling fluid having a brine salinity of around 150K (150,000 parts-per-million (ppm)), the curve 404 depicts a variation in the impedance due to a drilling fluid having a brine salinity of around 200K (200,000 ppm), and the curve 406 depicts a variation in the impedance due to a drilling fluid having a brine salinity of around 250K (250,000 ppm). In each case, the drilling fluid samples have a mud weight of around 10 ppg, an OWR of around 95/5, and a LGS weight of 0 g.

Figure 5:
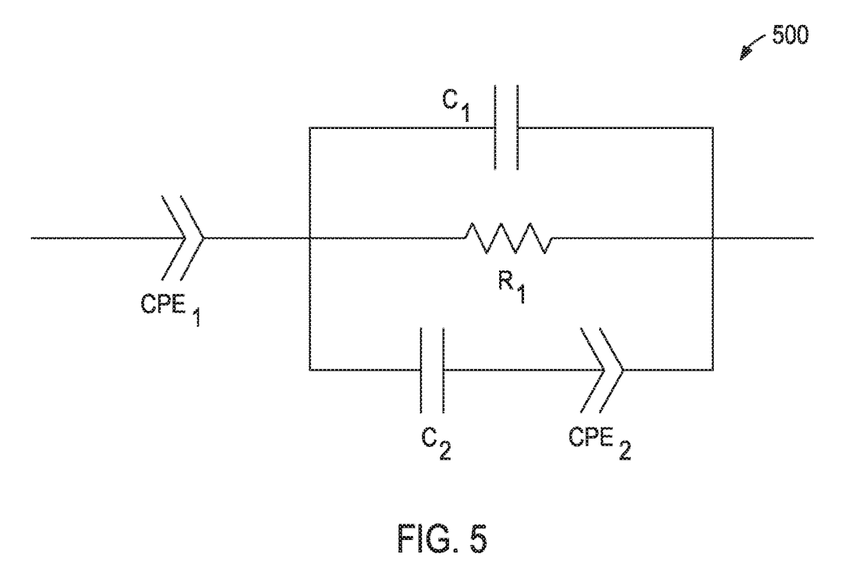
FIG. 5 illustrates an equivalent circuit model for simulating the frequency responses in FIGS. 1-4.

The impedance of the sample drilling fluids depicted in plots 100-400 may be simulated using an equivalent circuit model. FIG. 5 illustrates an equivalent circuit model 500 for simulating the frequency responses of the sample drilling fluids depicted in plots 100-400 of FIGS. 1-4, respectively, for different values of OWR, LGS weight, mud density, and brine salinity. Any equivalent circuit model that can singularly simulate (model) the frequency responses for all the different drilling fluid properties in FIGS. 1-4 may be used.

As illustrated, the equivalent circuit model 500 is composed of various model elements including a first capacitor C1, a second capacitor C2, a resistor R1, and first and second constant phase elements CPE1 and CPE2, respectively. The equivalent circuit impedance ($Z_{eq}$) of the equivalent circuit model 500 is given by:

$$Z_{eq} = Z_{CPE1} + \frac{Z_{C1}Z_{R1}(Z_{C2} + Z_{CPE2})}{Z_{C1}Z_{C2} + Z_{C1}Z_{CPE2} + Z_{C1}Z_{R1} + Z_{C2}Z_{R1} + Z_{CPE2}Z_{R1}}$$

where $Z_{C1}$, $Z_{C2}$, $Z_{R1}$, $Z_{CPE1}$, $Z_{CPE2}$ represent the impedances of the capacitors C1 and C2, resistor R1, and constant phase elements CPE1 and CPE2, respectively. The complex impedances for each model element are given by:

$$Z_{R1} = \omega R_1$$

$$Z_{C1} = \frac{1}{i\omega C1}$$

$$Z_{C2} = \frac{1}{i\omega C2}$$

$$Z_{CPE1} = \frac{1}{p_1(i\omega)^{n_1}}$$

$$Z_{CPE2} = \frac{1}{p_2(i\omega)^{n_2}}$$

The capacitive or resistive nature of the constant phase elements CPE1 and CPE2 is determined based on the values of n1 and n2. When n1=1, CPE1 represents an ideal capacitor and p1 represents the value of the capacitance of the capacitor CPE1. When n1=0, CPE1 represents an ideal resistor and p1 represents the value of the resistance of the resistor CPE1. For a value of n1 between 0 and 1 (0<n1<1), CPE1 represents a non-ideal capacitor. Similarly, when n2=1, CPE2 represents an ideal capacitor and p2 represents the value of the capacitance of the capacitor CPE2 and when n2=0, CPE2 represents an ideal resistor and p2 represents the value of the resistance of the resistor CPE2. For a value of n2 between 0 and 1 (0<n2<1), CPE2 represents a non-ideal capacitor.

In an example, the values of each model element C1, C2, R1, CPE1, and CPE2 of the equivalent circuit model 500 may be determined using a complex nonlinear least-square fitting procedure that minimizes a desired objective function. For example, the objective function may be given by:

$$\text{minSum} = \sum_{k=1}^{N} w_k \{[Z'(\omega_k) - Z'_{eq}(\omega_k)]^2 + [Z''(\omega_k) - Z''_{eq}(\omega_k)]^2\}$$

where k represents the $k^{th}$ measured data point at angular frequency $\omega_k$, Z' is the real part of the measured impedance of drilling fluid obtained from a wellbore, Z" is the imaginary part of the measured impedance of the drilling fluid obtained from the wellbore, $w_k$ is an optional weight used at each data point, $Z'_{eq}$ is the real part of the equivalent circuit impedance, and $Z''_{eq}$ is the imaginary part of the equivalent circuit impedance.

In order to obtain the real and imaginary values Z' and Z" of the measured impedance, a portion of the drilling fluid, a property of which is to be determined, is obtained from the wellbore of interest and an impedance thereof is measured using one or more desired impedance measurement systems (e.g., a LCR meter). The values of Z' and Z" are then obtained from the measured impedance data.

After the values of the model elements C1, C2, R1, CPE1, and CPE2 have been determined, a correlation between individual model elements C1, C2, R1, CPE1, and CPE2 and the drilling fluid properties desired to be measured is established.

Figure 6:
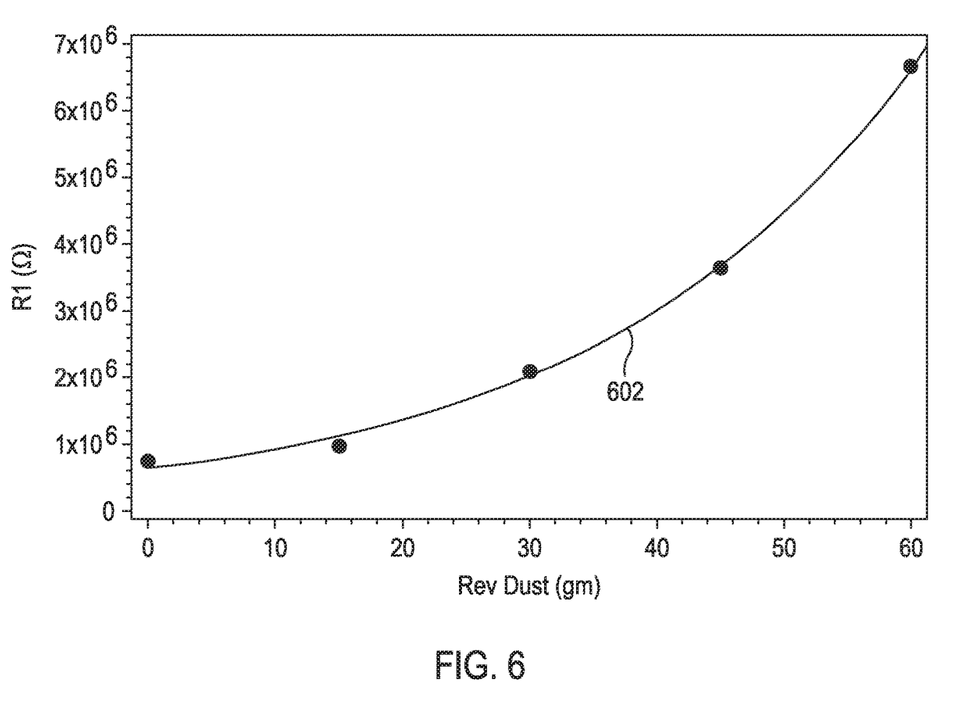
FIG. 6 illustrates an example calibration curve correlating a model resistance of the equivalent circuit model in FIG. 5 and the REV DUST® weight.

FIG. 6 illustrates an example calibration curve 602 correlating the model element resistance R1 and the REV DUST® weight. As mentioned above, the weight of low gravity solids (LGS) in the drilling fluids is simulated using REV DUST®. In FIG. 6, the calibration curve 602 has been approximated by an exponential function $R_1 = a \cdot e^{b \cdot RD}$, where a=620282, b=0.03984, and RD represents the REV DUST® weight.

Figure 7:
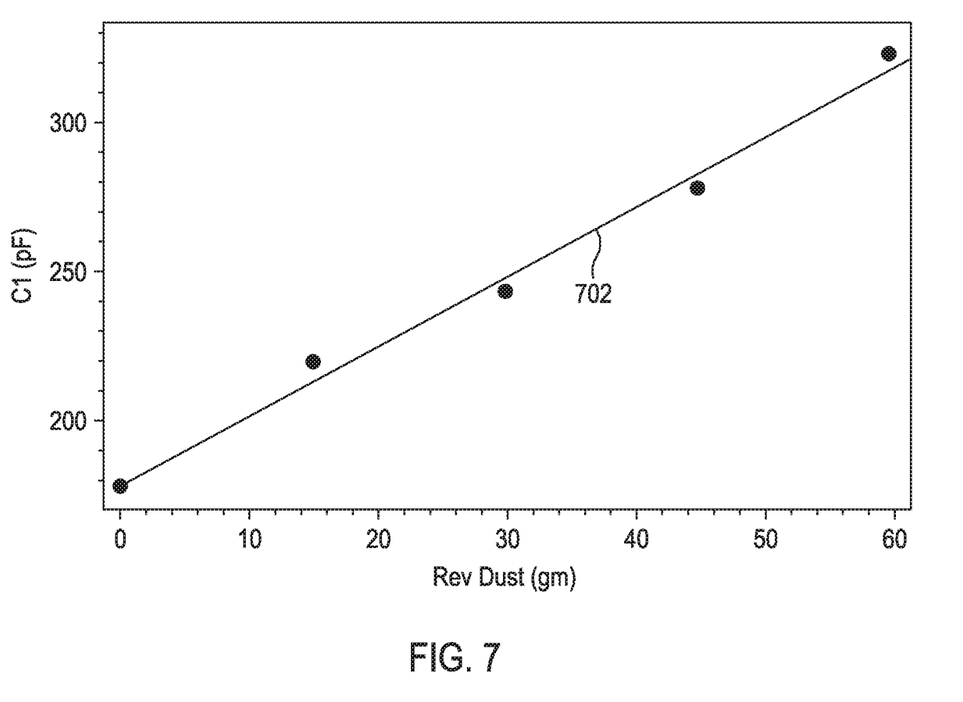
FIG. 7 illustrates an example calibration curve correlating a model capacitance of the equivalent circuit model in FIG. 5 and the REV DUST® weight.

Similarly, a correlation between the capacitance of the first capacitor C1 and the REV DUST® weight may also be determined. FIG. 7 illustrates an example calibration curve 702 correlating the capacitance of the first capacitor C1 and the REV DUST® weight. The calibration curve 702 indicates a linear correlation between the capacitance of the first capacitor C1 and the REV DUST® weight, and is approximated by the linear function $C1 = 0.1876 + 2.36 \times 10^{-3} \cdot RD$.

Based on these established correlations, the LGS weight in the drilling fluid from the wellbore may be determined using an inversion process. For example, from the measured impedance of the drilling fluid, the resistance value (real part of the impedance) may be determined. The LGS weight corresponding to the resistance value can then be obtained from the calibration curve 602 of FIG. 6. Alternatively, from the imaginary part of the impedance, the reactance value can be determined. The capacitance value is then obtained from the reactance value. The capacitance value can be used in the calibration curve 702 of FIG. 7 to determine the LGS weight.

It should be noted that the correlations between other model elements C2, CPE1, and CPE2 and the REV DUST® weight may also be determined in a similar manner. Further, correlations between one or more model elements C1, C2, R1, CPE1, and CPE2 and one or more of mud density, brine salinity, and oil/water ratio may also be determined to obtain the values of the mud density, brine salinity, and oil/water ratio of the drilling fluid sample from the wellsite.

In an embodiment, results from two or more correlations may be combined to obtain a more accurate value of one or more drilling fluid properties. For example, by combining the REV DUST® weight obtained from the calibration curves in FIGS. 6 and 7, the experimental and numerical inversion uncertainties may be minimized.

The electrochemical impedance spectroscopy (EIS) of fluids is dependent on a variety of fluid properties such as base oil types, viscosifier types, etc. In an embodiment, a laboratory generated EIS calibration table can be used. For example, the calibration table may include different values of the model element resistance R1 and corresponding REV DUST® weight values for a given viscosifier concentration in drilling fluid. Thus, the measured resistance value for a matching drilling fluid formulation may be compared to the resistance R1 values in calibration table to find the corresponding LGS weight.

As mentioned above, the equivalent circuit model 500 is not unique. Accordingly, in an embodiment, an equivalent circuit model may be selected from a collection of optimized equivalent circuit models during the EIS analysis (e.g., when performed in the field) to minimize the computation time. For example, an equivalent circuit model that shows a good fitting to all the experimental data obtained during the EIS analysis using minimum parameters may be selected. However, it will be understood by one skilled in the art that two or more equivalent circuit models that show a good fitting may be identified, and a model that best fits the measured data or a model having circuit elements whose values are most sensitive to desired fluid properties may be selected.

Figure 8:
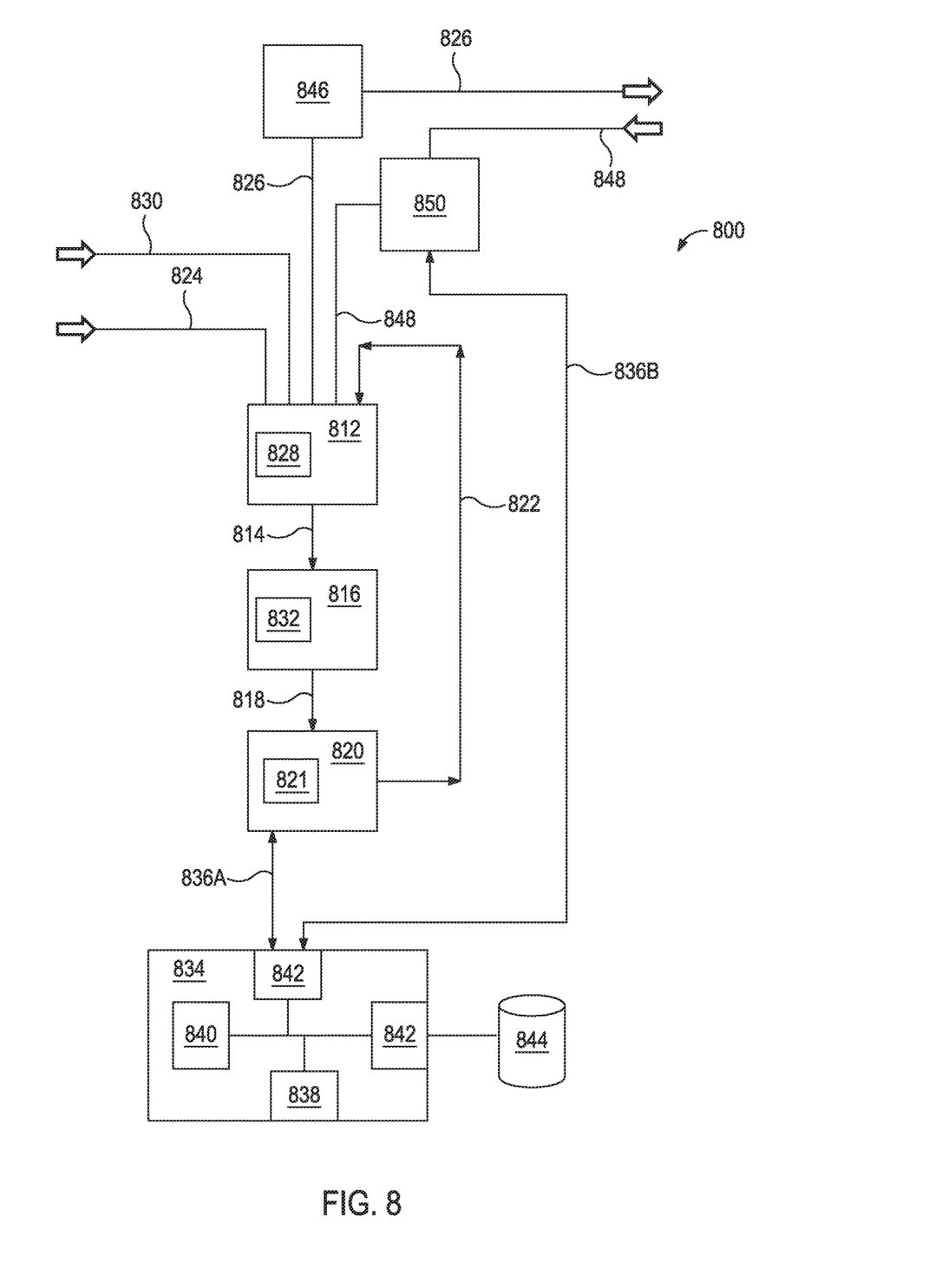
FIG. 8 illustrates a block flow diagram of a drilling fluid monitoring and handling system for determining one or more properties of drilling fluids using the principles of the present disclosure.

FIG. 8 illustrates a block diagram of a drilling fluid monitoring and handling system 800 for determining one or more properties of drilling fluids, such as LGS weight, mud density, brine salinity, and oil/water ratio using the principles of the present disclosure. As illustrated, the fluid monitoring and handling system 800 may generally include a mud pit 812, a fluid supply system 816, and a fluid analysis system 820. A portion of the drilling fluid from the mud pit 812 may be fed via a mud pit line 814 to the fluid supply system 816. The portion of the drilling fluid may then be fed via fluid supply line 818 to the fluid analysis system 820, which may be configured to measure the impedance of the portion of the drilling fluid supplied thereto. The fluid analysis system 820 may analyze the drilling fluid using the example method disclosed above with reference to FIGS. 1-7. After fluid analysis, the portion of the drilling fluid may be returned to mud pit 812 via a return line 822.

The mud pit 812 may be any vessel suitable for holding a drilling fluid. For example, the mud pit 812 may comprise a container such as a drum or tank, or a series of containers that may or may not be connected. The mud pit 812 may be supplied with the drilling fluid from an initial drilling fluid supply line 830 that provides an initial supply of drilling fluid to the mud pit 812. However, the initial supply of drilling fluid does not imply that the drilling fluid has not been recycled or circulated in a wellbore, but simply indicates that this supply is not presently being circulated or otherwise used in the wellbore. A mud-mixing hopper (not explicitly shown) may be coupled to the initial drilling fluid supply line 830 and used to mix a new drilling fluid before the drilling fluid is sent to the mud pit 812.

Drilling fluid additives (e.g., emulsifiers, viscosifiers, density modifying agents, and the like) may be added via a drilling fluid additive supply line 824 to the mud pit 812, if desired, and based on the analysis provided by the fluid analysis system 820. Alternatively or additionally, in an example, the results of the analysis may be used to modify the manufacturing process of the drilling fluid. After the drilling fluid additives have been added to the drilling fluid, the drilling fluid may be retested using the fluid analysis system 820 to verify the drilling fluid was correctly formulated or the drilling fluid may be sent to the wellbore for use in drilling operations via a wellbore line 826. In determining the fluid additives to be added, the fluid analysis system 820 may also consider measurements obtained from the wellbore regarding the formation features (e.g., a salt stream) that the drilling fluid may interact with during a drilling operation. Alternatively, if the wellbore information is previously known, then the drilling fluid may be formulated in anticipation of said formation features. The fluid analysis system 820 may be used to validate that the correct anticipatory formulation has been achieved prior to drilling operations.

The mud pit 812 may include a mixing system 828 to mix the contents of the mud pit 812 as well as any drilling fluid additives. For instance, the mixing system 828 may mix the drilling fluid in the mud pit 812 with drilling fluid from the initial drilling fluid supply line 830, drilling fluid from the return line 822, drilling fluid additives, additional non-aqueous fluids, aqueous fluids or combinations thereof. In general, the mixing system 828 may be configured to prevent solids within the drilling fluid from settling. The mixing system 828 may use any suitable mixing technique for mixing of the drilling fluid. For instance, the mixing system 828 may comprise a static mixer, dynamic mixer, or other suitable mixer. The mud pit 812 may further include suitable pumping equipment to pump the drilling fluid in the mud pit 812 to the fluid supply system 816 via the mud pit line 814 or to pump the drilling fluid to the wellbore via a wellbore line 826.

The drilling fluid in the fluid supply system 816 may be conditioned. For example, the fluid supply system 816 may comprise filtering equipment to remove solids, such as calcium carbonate and/or lost circulation materials, from the received drilling fluid. The fluid supply system 816 may include at least one fluid supply pumping system 832 that may be any type of pump suitable for pumping the drilling fluid from the fluid supply system 816 to the fluid analysis system 820 via the fluid supply line 818. For example, the fluid supply pumping system 832 may be or include a mud pump or analogous pump and/or pumping system. The fluid supply system 816 may pump the drilling fluid in a continuous or non-continuous manner.

The fluid analysis system 820 may analyze the portion of the drilling fluid in a continuous or non-continuous manner, as desired, and based on whether flow through fluid analysis system 820 is continuous or non-continuous. The fluid analysis system 820 may include one or more instruments 821 for measuring the impedance of the drilling fluid. For example, the instrument(s) 821 may include a measurement probe, an optical measuring system, an imaging measuring system, a laser measuring system, an ultrasound measuring system, a pH measuring system, a density measurement system, an emulsion stability system, a rheology measurement system, a titration system, or any combination thereof. In an example, the impedance of the drilling fluid may be determined using the Series 1920 Precision LCR Meter from QuadTech, Inc.

Although illustrated as being included in the fluid analysis system 820, examples disclosed herein contemplate the placement of the one or more instruments 821 at any point in the fluid monitoring and handling system 800. For example, one or more instruments 821 may alternatively be placed in the fluid reconditioning system 850 (discussed below), the mud pit 812, as well as within the wellbore or in an exit conduit from the wellbore. As such, examples disclosed herein contemplate measuring the impedance of the drilling fluid at any point in the drilling fluid handling process, so that the drilling fluid may be monitored and/or subsequently adjusted as desired.

The analysis performed by fluid analysis system 820 may be performed in collaboration with a computer system 834 communicably coupled thereto. As illustrated, the computer system 834 may be an external component of the fluid analysis system 820, however, the computer system 834 may alternatively comprise an internal component of the fluid analysis system 820, without departing from the scope of the disclosure. The computer system 834 is connected to the fluid analysis system 820 via a communication link 836A. The communication link 836A may include a direct (wired) connection, a private network, a virtual private network, a local area network, a WAN (e.g., an Internet-based communication system), a wireless communication system (e.g., a satellite communication system, telephones), any combination thereof, or any other suitable communication link.

The computer system 834 may be any suitable data processing system including, but not limited to, a computer, a handheld device, or any other suitable device. The computer system 834 may include a processor 838 and a non-transitory computer readable storage medium 840 communicatively coupled to the processor 838. The processor 838 may comprise one central processing unit or may be distributed across one or more processors in one or more locations. Examples of a non-transitory computer readable storage medium 840 include random-access memory (RAM) devices, read-only memory (ROM) devices, optical devices (e.g., CDs or DVDs), disk drives, and the like. The non-transitory computer readable storage medium 840 may store computer readable program code that may be executed by the processor 838 to process and analyze the measurement data generated by fluid analysis system 820, adjust the parameters of the fluid monitoring and handling system 800, and/or operate a part or whole of the fluid monitoring and handling system 800. Additionally, the program code may be executed by the processor 838 to generate the frequency responses of one or more sample fluids, obtain an equivalent circuit model for modeling the frequency responses, and generate a correlation between individual model elements of the equivalent circuit model and the properties of the one or more sample fluids. Further, from the impedance of the drilling fluid measured by the fluid analysis system 820, the program code may be executed by the processor 838 to determine one or more properties of drilling fluids using the correlation between the individual model elements of the equivalent circuit model and the properties of the one or more sample fluids.

The computer system 834 may further include one or more input/output ("I/O") interface(s) 842 communicatively coupled to the processor 838. The I/O interface(s) 842 may be any suitable system for connecting the computer system 834 to a communication link, such as a direct connection, a private network, a virtual private network, a local area network, a wide area network ("WAN"), a wireless communication system, or combinations thereof; a storage device, such as storage 844; an external device, such as a keyboard, a monitor, a printer, a voice recognition device, or a mouse; or any other suitable system. The storage 844 may store data required by the fluid analysis system 820 for performing fluid analysis. For instance, the storage 844 may store a collection of equivalent circuit models that may be used during the EIS analysis. The storage 844 may be or include compact disc drives, floppy drives, hard disks, flash memory, solid-state drives, and the like. Those of ordinary skill in the art will appreciate that suitable data processing systems may comprise additional, fewer, and/or different components than those described for computer system 834.

Data processing and analysis software native to the fluid analysis system 820 and/or installed on the computer system 834 may be used to analyze the data generated by fluid analysis system 820. This procedure may be automated such that the analysis happens without the need for operator input or control. Further, the operator may select from several previously input parameters or may be able to recall previously measured data. Any of the data may be transferred and/or stored on an external memory device (e.g., a USB drive), if desired.

With continued reference to FIG. 8, if a drilling fluid is of a satisfactory formulation, the drilling fluid may be pumped to a mud pump 846 via the wellbore line 826 (e.g., a suction line) to pump the drilling fluid into the wellbore (not shown). The mud pump 846 may be any type of pump or pumping system useful for circulating a drilling fluid into a subterranean formation under a sufficient pressure. The drilling fluid that has been circulated within the wellbore may be returned to the mud pit 812 via a circulated drilling fluid return line 848 and provided to a fluid reconditioning system 850 to condition the circulated drilling fluid prior to returning it to the mud pit 812. The fluid reconditioning system 850 may be or include one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The fluid reconditioning system 850 may further include one or more sensors, gauges, pumps, compressors, and the like used to monitor, regulate, and/or recondition the drilling fluid and various additives added thereto. After the drilling fluid has been reconditioned, the drilling fluid may be returned to the mud pit 812 via the circulated drilling fluid return line 848.

A communication link 836B may link the fluid reconditioning system 850 to the computer system 834. The communication link 836B may include a direct (wired) connection, a private network, a virtual private network, a local area network, a WAN (e.g., an Internet-based communication system), a wireless communication system (e.g., a satellite communication system, telephones), combinations thereof, or any other suitable communication link. The communication link 836B may allow the computer system 834 to adjust the parameters of the fluid reconditioning system 850 based on the analysis performed by the fluid analysis system 820. In an example, the computer system 834 may also evaluate the efficiency of operation of the drilling fluid monitoring and handling system 800 based on the analysis by the fluid analysis system 820. For instance, the analysis of the drilling fluid may be used to determine the operational efficiencies of one or more of the drilling fluid handling systems including fluid supply system 816, the mud pump 846, and the fluid reconditioning system 850. Further, the fluid analysis system 820 may be used to adjust the amount of and type of additives used and supplied via the drilling fluid additive supply line 824. This process may be conducted via a separate communication link with the vessel or vessels in which the drilling fluid additives may be stored (not shown).

Figure 9:
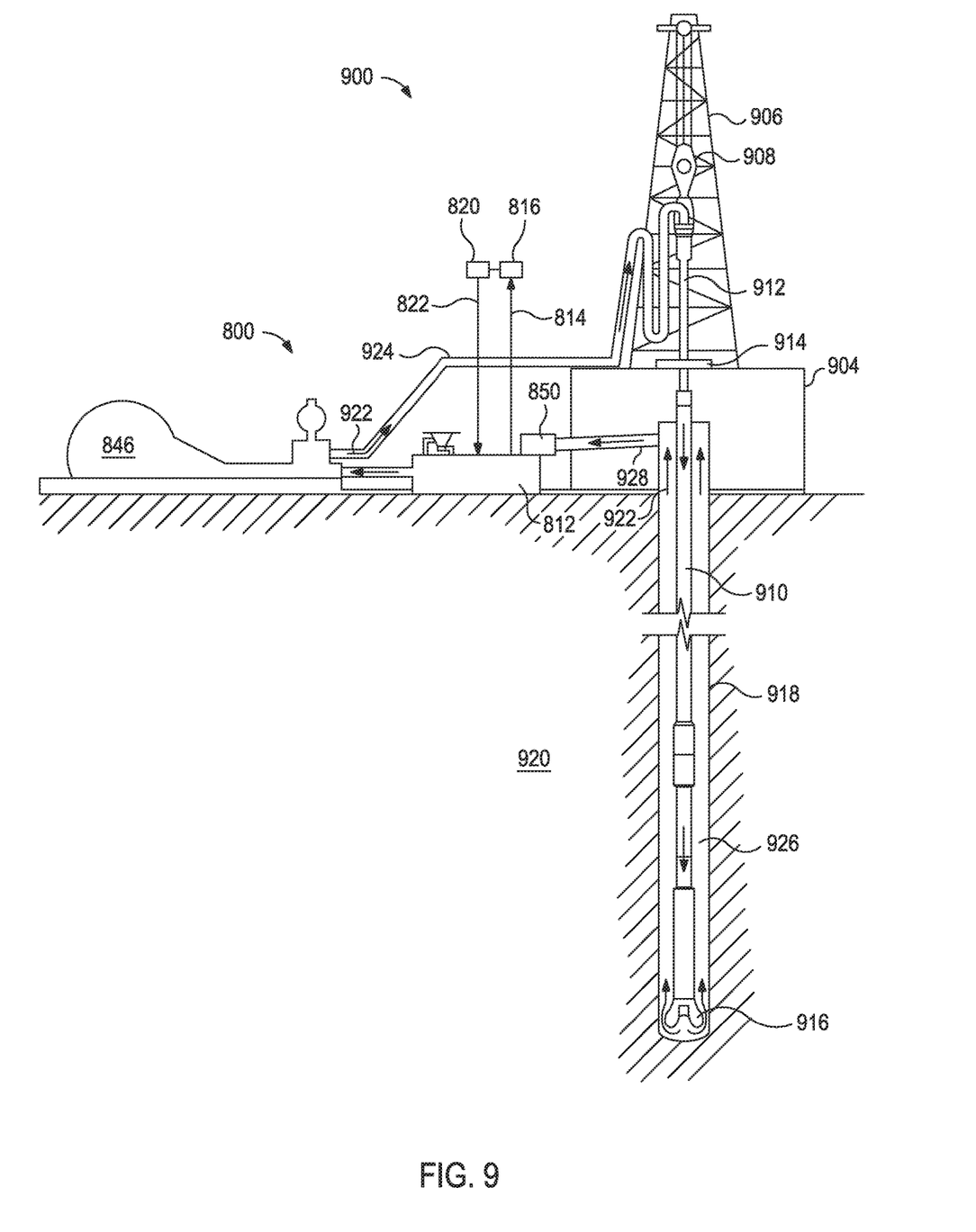
FIG. 9 illustrates an example wellbore drilling assembly that employs the fluid monitoring and handling system of FIG. 8 for determining one or more properties of the drilling fluid.

FIG. 9 illustrates an example drilling assembly 900 that may employ the fluid monitoring and handling system 800 of FIG. 8 described herein to determine one or more properties of the drilling fluid. It should be noted that while FIG. 9 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling assembly 900 may include a drilling platform 904 that supports a derrick 906 having a traveling block 908 for raising and lowering a drill string 910. The drill string 910 may include, but is not limited to, drill pipe and coiled tubing, as generally known to those skilled in the art. A kelly 912 may support the drill string 910 as it may be lowered through a rotary table 914. A drill bit 916 may be attached to the distal end of the drill string 910 and may be driven either by a downhole motor and/or via rotation of the drill string 910 from the well surface. Without limitation, the drill bit 916 may include, roller cone bits, PDC bits, natural diamond bits, any hole openers, reamers, coring bits, and the like. As the drill bit 916 rotates, it may create a wellbore 918 that penetrates various subterranean formations 920.

The drilling assembly 900 may further include the fluid monitoring and handling system 800 as generally described herein. The mud pump 846 of the fluid monitoring and handling system 800 representatively includes any conduits, pipelines, trucks, tubulars, and/or pipes used to fluidically convey the drilling fluid 922 downhole, any pumps, compressors, or motors (e.g., topside or downhole) used to drive the drilling fluid 922 into motion, any valves or related joints used to regulate the pressure or flow rate of the drilling fluid 922, and any sensors (e.g., pressure, temperature, flow rate, etc.), gauges, and/or combinations thereof, and the like.

The mud pump 846 may circulate the drilling fluid 922 through a feed pipe 924 and to the kelly 912, which conveys the drilling fluid 922 downhole through the interior of the drill string 910 and through one or more orifices in the drill bit 916. The drilling fluid 922 may then be circulated back to the surface via an annulus 926 defined between the drill string 910 and the walls of the wellbore 918. At the surface, the recirculated or spent drilling fluid 922 may be conveyed to the fluid reconditioning system 850 via an interconnecting flow line 928. After passing through the fluid reconditioning system 850, a "cleaned" drilling fluid 922 may be deposited into a nearby mud pit 812. While illustrated as being arranged at the outlet of the wellbore 918 via the annulus 926, those skilled in the art will readily appreciate that the fluid reconditioning system 850 may be arranged at any other location in the drilling assembly 900 to facilitate its proper function, without departing from the scope of the scope of the disclosure.

Referring still to FIG. 9, the fluid monitoring and handling system 800 may further include the fluid supply system 816 and the fluid analysis system 820, which may be disposed on a skid supported on the drilling platform 904. The fluid analysis system 820 may, for example, continuously or intermittently measure the impedance of the drilling fluid 922. As illustrated, the drilling fluid 922 may be taken from the mud pit 812 via the mud pit line 814 and an analyzed drilling fluid may be returned to the mud pit 812 via the return line 822. Alternatively, the impedance of the drilling fluid 922 may be measured, recorded, and/or analyzed at fluid reconditioning system 850 or even while in the wellbore if desired.

In an example, the drilling fluid 922 may be measured, recorded, and/or analyzed at two or more locations in the drilling assembly 900. For instance, the impedance of the drilling fluid 922 may be measured when being pumped downhole and when returning to the surface (e.g., the spent drilling fluid). The difference in the two measurements may provide insight into fluid composition changes that includes a time delay profile because of the volume of the wellbore and the distance travelled by the drilling fluid in the wellbore. These changes may include fluid components lost to the formation, solids incorporated into the fluid from the formation and cutting attrition, and/or an influx of wellbore fluid(s). The differential measurement provides an indication of the changes in fluid composition due to any wellbore process or other processes performed on the surface and the quantitative information to make any appropriate changes to the fluid system or to make operational changes.

Thus, the fluid monitoring and handling system 800 may advantageously monitor the drilling fluid properties using the example method disclosed herein and generate automatic warnings to the personnel when the drilling fluid properties deviate from preset safety margins.

Figure 10:
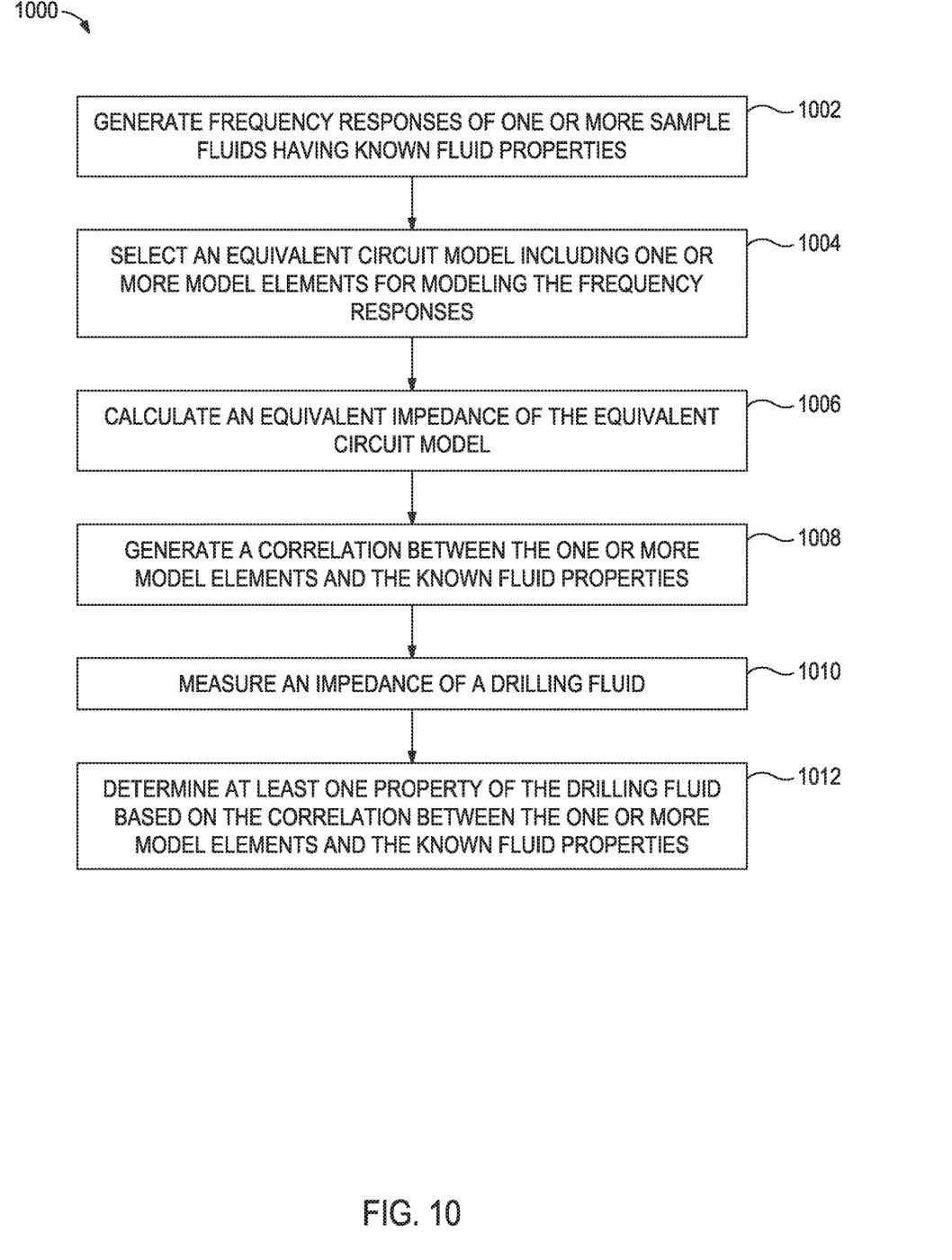
FIG. 10 is a flow chart of a method for determining a property of a drilling fluid.

FIG. 10 is a flow chart of a method 1000 for determining a property of a drilling fluid. The method 1000 may include generating frequency responses of one or more sample fluids having known fluid properties, as at 1002, selecting an equivalent circuit model including one or more model elements for modeling the frequency responses, as at 1004, calculating an equivalent impedance of the equivalent circuit model, as at 1006, generating a correlation between the one or more model elements and the known fluid properties, as at 1008, measuring an impedance of a drilling fluid, as at 1010, determining at least one property of the drilling fluid based on the correlation between the one or more model elements and the known fluid properties, as at 1012.

Embodiments disclosed herein include:

A. A method that includes generating frequency responses of one or more sample fluids having known fluid properties; selecting an equivalent circuit model for modeling the frequency responses, the equivalent circuit model including one or more model elements; calculating an equivalent impedance of the equivalent circuit model; generating a correlation between the one or more model elements and the known fluid properties; measuring an impedance of a drilling fluid; and determining at least one property of the drilling fluid based on the correlation between the one or more model elements and the known fluid properties.

B. A system that includes a fluid monitoring and handling system to determine one or more properties of a drilling fluid; and a computer system including a processor and a non-transitory computer readable storage medium, the computer system being communicatively coupled to the fluid monitoring and handling system, and the computer readable storage medium storing a computer readable program code that when executed by the processor causes the computer system to: generate frequency responses of one or more sample fluids having known fluid properties; select an equivalent circuit model for modeling the frequency responses, the equivalent circuit model including one or more model elements; calculate an equivalent impedance of the equivalent circuit model; generate a correlation between the one or more model elements and the known fluid properties; measure an impedance of the drilling fluid; and determine at least one property of the drilling fluid based on the correlations between the one or more model elements and the known fluid properties.

Each of embodiments A and B may have one or more of the following additional elements in any combination: Element 1: further comprising calculating values of the one or more model elements that minimize a desired objective function; and generating the correlation using the values. Element 2: further comprising generating two or more correlations between two or more different model elements and a same known property; determining the at least one property of the drilling fluid based on the two or more correlations and thereby obtain two values of the property of the drilling fluid; and combining the two values of the property of the drilling fluid to minimize uncertainties in determining the at least one property of the drilling fluid. Element 3: wherein determining the equivalent circuit model comprises selecting the equivalent circuit model from a collection of equivalent circuit models. Element 4: further comprising determining an efficiency of operation of one or more drilling fluid handling systems based on the at least one property of the drilling fluid. Element 5: wherein determining the at least one property of the drilling fluid includes determining one or more of an oil/water ratio (OWR), a low gravity solid (LGS) content, a mud density, and a brine salinity of the drilling fluid. Element 6: further comprising adjusting the at least one property of the drilling fluid in response to the at least one property of the drilling fluid as determined. Element 7: further comprising adjusting the at least one property of the drilling fluid by adding drilling fluid additives to the drilling fluid. Element 8: further comprising circulating the drilling fluid into and out of a wellbore.

Element 9: wherein executing the program code further causes the computer system to calculate values of the one or more model elements that minimize a desired objective function; and generate the correlation using the values. Element 10: wherein executing the program code further causes the computer system to generate two or more correlations between two or more different model elements and a same known property; determine the property of the drilling fluid based on the two or more correlations and thereby obtain two values of the property of the drilling fluid; and combine the two values of the at least one property of the drilling fluid to minimize uncertainties in determining the at least one property of the drilling fluid. Element 11: wherein executing the program code further causes the computer system to select the equivalent circuit model from a collection of equivalent circuit models. Element 12: wherein executing the program code further causes the computer system to determine an efficiency of operation of one or more components of the fluid monitoring and handling system based on the at least one property of the drilling fluid. Element 13: wherein executing the program code further causes the computer system to determine one or more of the at least one property including an oil/water ratio (OWR), a low gravity solid (LGS) content, a mud density, and a brine salinity of the drilling fluid. Element 14: wherein executing the program code further causes the computer system to adjust the at least one property of the drilling fluid based on the at least one property of the drilling fluid as determined. Element 15: wherein executing the program code further causes the computer system to actuate the fluid monitoring and handling system to adjust the at least one property of the drilling fluid by adding drilling fluid additives to the drilling fluid. Element 16: wherein executing the program code further causes the computer system to actuate the fluid monitoring and handling system to circulate the drilling fluid into and out of a wellbore.

By way of non-limiting example, exemplary combinations applicable to A and B include: Element 6 with Element 7; and Element 14 with Element 15.

Therefore, the present embodiments are well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A method, comprising:
   generating frequency responses of one or more sample fluids having known fluid properties;
   selecting an equivalent circuit model for modeling the frequency responses, the equivalent circuit model including two or more model elements;
   calculating an equivalent impedance of the equivalent circuit model;
   performing a calibration on at least one model element from the two or more model elements of the equivalent circuit model to form a calibrated resistance or a calibrated capacitance;
   generating two or more correlations between the two or more model elements and a same known fluid property, wherein at least one correlation from the two or more correlations is between the calibrated resistance or the calibrated capacitance and at least one model element;
   measuring an impedance of a drilling fluid; and
   determining at least one property of the drilling fluid based on the two or more correlations between the two or more model elements and the known fluid property.

2. The method of claim 1, further comprising:
   calculating values of the two or more model elements that minimize a desired objective function; and
   generating the two or more correlations using the values.

3. The method of claim 1, wherein determining the equivalent circuit model comprises selecting the equivalent circuit model from a collection of equivalent circuit models.

4. The method of claim 1, further comprising determining an efficiency of operation of one or more drilling fluid handling systems based on the at least one property of the drilling fluid.

5. The method of claim 1, wherein determining the at least one property of the drilling fluid includes determining at least one of an oil/water ratio (OWR), a low gravity solid (LGS) content, a mud density, and a brine salinity of the drilling fluid.

6. The method of claim 1, further comprising circulating the drilling fluid into and out of a wellbore.

7. The method of claim 1, further comprising extending a wellbore through a subterranean formation.

8. The method of claim 1, further comprising adjusting the at least one property of the drilling fluid in response to the at least one property of the drilling fluid as determined.

9. The method of claim 8, further comprising adjusting the at least one property of the drilling fluid by adding drilling fluid additives to the drilling fluid.

10. A system, comprising:
    a fluid monitoring and handling system to determine one or more properties of a drilling fluid; and
    a computer system including a processor and a non-transitory computer readable storage medium, the computer system being communicatively coupled to the fluid monitoring and handling system, and the computer readable storage medium storing a computer readable program code that when executed by the processor causes the computer system to:
    generate frequency responses of one or more sample fluids having known fluid properties;
    select an equivalent circuit model for modeling the frequency responses, the equivalent circuit model including two or more model elements;
    calculate an equivalent impedance of the equivalent circuit model;
    perform a calibration on at least one model element from the two or more model elements of the equivalent circuit model to form a calibrated resistance or a calibrated capacitance;
    generate two or more correlations between the two or more model elements and the known fluid properties, wherein at least one correlation from the two or more correlations is between the calibrated resistance or the calibrated capacitance and at least one model element;
    measure an impedance of the drilling fluid; and
    determine at least one property of the drilling fluid based on the two or more correlations between the two or more model elements and a same known fluid property.

11. The system of claim 10, wherein executing the program code further causes the computer system to:
    calculate values of the two or more model elements that minimize a desired objective function; and
    generate the two or more correlations using the values.

12. The system of claim 10, wherein executing the program code further causes the computer system to select the equivalent circuit model from a collection of equivalent circuit models.

13. The system of claim 10, wherein executing the program code further causes the computer system to determine an efficiency of operation of one or more components of the fluid monitoring and handling system based on the at least one property of the drilling fluid.

14. The system of claim 10, wherein executing the program code further causes the computer system to determine the at least one property including an oil/water ratio (OWR), a low gravity solid (LGS) content, a mud density, and a brine salinity of the drilling fluid.

15. The system of claim 10, wherein executing the program code further causes the computer system to actuate the fluid monitoring and handling system to circulate the drilling fluid into and out of a wellbore.

16. The system of claim 10, wherein executing the program code further causes the computer system to adjust the at least one property of the drilling fluid based on the at least one property of the drilling fluid as determined.

17. The system of claim 16, wherein executing the program code further causes the computer system to actuate the fluid monitoring and handling system to adjust the at least one property of the drilling fluid by adding drilling fluid additives to the drilling fluid.

\* \* \* \* \*